(12) United States Patent
Stancer et al.

(10) Patent No.: US 7,925,322 B2
(45) Date of Patent: Apr. 12, 2011

(54) SHROUD-BASED ELECTRODES HAVING VENTED GAPS

(75) Inventors: Christopher C. Stancer, Prescott, WI (US); John C. Mertz, Maple Grove, MN (US); Thomas H. Adamski, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 286 days.

(21) Appl. No.: 11/380,811

(22) Filed: Apr. 28, 2006

(65) Prior Publication Data

US 2007/0255158 A1 Nov. 1, 2007

(51) Int. Cl.
*A61B 1/04* (2006.01)
(52) U.S. Cl. .................................................. 600/377
(58) Field of Classification Search .................. 600/372, 600/373, 374, 377; 607/116, 119, 129
See application file for complete search history.

(56) References Cited

U.S. PATENT DOCUMENTS

| | | | |
|---|---|---|---|
| 3,983,867 A | 10/1976 | Case | |
| 4,023,565 A | 5/1977 | Ohlsson | |
| 4,082,086 A | 4/1978 | Page et al. | |
| 4,121,576 A | 10/1978 | Greensite | |
| 4,170,227 A | 10/1979 | Feldman et al. | |
| 4,263,919 A | 4/1981 | Levin | |
| 4,310,000 A | 1/1982 | Lindemans | |
| 4,313,443 A | 2/1982 | Lund | |
| 4,506,680 A | 3/1985 | Stokes | |
| 4,593,702 A | 6/1986 | Kepski et al. | |
| 5,331,966 A | 7/1994 | Bennett et al. | |
| 6,205,358 B1 | 3/2001 | Haeg et al. | |
| 6,512,940 B1 * | 1/2003 | Brabec et al. | 600/374 |
| 6,522,915 B1 * | 2/2003 | Ceballos et al. | 600/509 |
| 6,997,949 B2 | 2/2006 | Tuch | |
| 2002/0147488 A1 * | 10/2002 | Doan et al. | 607/122 |
| 2004/0122481 A1 * | 6/2004 | Tidemand et al. | 607/37 |
| 2006/0217777 A1 | 9/2006 | Strom et al. | |
| 2006/0217778 A1 | 9/2006 | Strom et al. | |

FOREIGN PATENT DOCUMENTS

WO WO0236000 A 5/2002

\* cited by examiner

*Primary Examiner* — Mark W Bockelman
*Assistant Examiner* — Roland Dinga
(74) *Attorney, Agent, or Firm* — Stephen W. Bauer; Reed A. Duthler

(57) ABSTRACT

Apparatus and method according to the disclosure relate to promoting flow of body fluids in and around and between a substantially planar cardiac-sensing electrode and a shroud member utilizing spacing therebetween and/or one or more apertures, notches, slots and the like. For example, a relatively recessed area or aperture formed in an exemplary resin-based shroud member includes apertures that cooperate to promote flow of body fluids therearound.

17 Claims, 6 Drawing Sheets

SHROUD-BASED ELECTRODES HAVING VENTED GAPS

CROSS REFERENCE TO RELATED APPLICATION

The present patent document is related to co-pending non-provisional patent application Ser. No. 11/085,843, entitled, "APPARATUS AND METHODS OF MONITORING CARDIAC ACTIVITY UTILIZING IMPLANTABLE SHROUD-BASED ELECTRODES," filed on 22 Mar. 2005 the contents of which are hereby incorporated by reference.

FIELD OF THE INVENTION

The present invention relates generally to implantable medical devices and more particularly to a subcutaneous multiple electrode sensing and recording system for acquiring electrocardiographic data and waveform tracings from an implanted medical device without the need for or use of surface (skin) electrodes. More particularly, the present invention relates to implantable devices that are equipped with a shroud member that includes at least one electrode operatively coupled to sense cardiac activity and configured to promote flow of body fluid in and around the electrode.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. For example, S-T segment changes can be used to detect an ischemic episode. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

Previous art describes how to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems, which combine surface EKG signals for artifact rejection.

The primary use for multiple electrode systems in the prior art is vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

With regard to various aspects of time-release of surface coatings and the like for chronically implanted medical devices, the following issued patents are incorporated herein by reference. U.S. Pat. No. 6,997,949 issued 14 Feb. 2006 and entitled, "Medical device for delivering a therapeutic agent and method of preparation," and U.S. Pat. No. 4,506,680 entitled, "Drug dispensing body implantable lead." In the former patent, the following is described (from the Abstract section of the '949 patent) as follows: A device useful for localized delivery of a therapeutic agent is provided. The device includes a structure including a porous polymeric material and an elutable therapeutic agent in the form of a solid, gel, or neat liquid, which is dispersed in at least a portion of the porous polymeric material. Methods for making a medical device having blood-contacting surface electrodes is also provided.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG. Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY OF THE INVENTION

The present invention provides a leadless subcutaneous (or submuscular) single or multiple-electrode array that provides various embodiments of a compliant surround shroud coupled to a peripheral portion of an implantable medical device (IMD). The shroud incorporates a plurality of substantially planar electrodes mechanically coupled within recessed portions of the shroud. These electrodes electrically couple to circuitry of an IMD and are adapted to detect cardiac activity of a subject. Temporal recordings of the detected cardiac activity are referred to herein as an extra-cardiac electrogram (EC-EGM). The recordings can be stored upon computer readable media within an IMD at various resolution (e.g., continuous beat-by-beat, periodic, triggered, mean value, average value, etc.). Real time or stored EC-EGM signals can be provided to remote equipment via telemetry. For example, when telemetry, or programming, head of an IMD programming apparatus is positioned within range of an IMD the programmer receives some or all of the EC-EGM signals.

The diverse materials contemplated by the instant invention can be applied using any of a variety of techniques such as by sputtering, spraying, thermal or piezoelectric ink jet printing, electron beam deposition, immersion techniques, CVD or the like. Some coatings, such as steroid-eluting materials, can become more important over time as such enhancing coatings can help as the electrodes (typically) become encapsulated in scar tissue and thus at least indirectly contact with the body tissue. Such indirect tissue contact can damp the cardiac signals thus negatively affecting the sensing and detection ability of uncoated electrode(s). As is known in the art steroids include any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins. The invention embraces all such variations of the foregoing.

Certain embodiments of the invention utilize substantially planar electrodes designed to promote the free flow of fluids such as body fluid and the like in and around the electrode and abutting or adjacent portions of a shroud structure. While perhaps viewed as counterintuitive, such fluid flow can advantageously promote circulation of agents of a body's own natural defenses and/or circulation of therapeutic substances ingested by a subject (e.g., antibiotics and the like). Thus, a possible source of irritation and/or infection can be continuously flushed thereby avoiding stagnation of body fluid that might have otherwise been trapped in and around components of the electrode and shroud member.

According to the invention, one or both of a recess (or aperture) of a shroud member and a plate-type electrode adapted to reside in the recess (or aperture) includes apertures, recesses, slots, notches and the like in order to promote ingress and egress of body fluids therethrough and to thereby reduce the presence of stagnant body fluid and thus possibility of infection.

The present invention provides improved apparatus and methods for reliably collecting EC-EGM signals for use or collection in conjunction with diverse IMDs (e.g., implantable pacemakers having endocardial leads, implantable cardioverter-defibrillators or ICDs, drug delivery pumps, subcutaneous ICDs, submuscular ICDs, brain stimulation devices, nerve stimulation devices, muscle stimulation devices and the like).

The invention can be implemented employing suitable sensing amplifiers, switching circuits, signal processors, and memory to process the EC-EGM signals collected between any selected pair or pairs of the electrodes deployed in an array around the periphery or surface of a housing of an IMD to provide a leadless, orientation-insensitive means for receiving the EC-EGM signals from the heart.

The shroud can comprise a non-conductive, bio-compatible material such as any appropriate resin-based material, urethane polymer, silicone, or relatively soft urethane that retains its mechanical integrity during manufacturing and prolonged exposure to body fluids. The shroud placed around the peripheral portions of an IMD can utilize a number of configurations (e.g., two, three, four recesses) for individual electrodes. However, a four-electrode embodiment appears to provide an improved signal-to-noise ratio than the three-electrode embodiment. And, embodiments having a single electrode pair appear much more sensitive to appropriate orientation of the device relative to the heart than embodiments having more than a single pair of electrodes. Of course, embodiments of the invention using more than four electrodes increase complexity without providing a significant improvement in signal quality.

Embodiments having electrodes connected to three sense-amplifiers that are hardwired to three electrodes can record simultaneous EC-EGM signals. Alternative embodiments employ electrodes on the face of the lead connector, or header module, and/or major planar face(s) of the pacemaker that may be selectively or sequentially coupled in one or more pairs to the terminals of one or more sense amplifiers to pick up, amplify and process the EC-EGM signals across each electrode pair. In one aspect, the EC-EGM signals from a first electrode pair are stored and compared to other electrode pair(s) in order to determine the optimal sensing vector. Following such an optimization procedure, the system can be programmed to chronically employ the selected subcutaneous EC-EGM signal vector.

Prior art patent U.S. Pat. No. 5,331,966 had electrodes placed on the face of the implanted pacemaker. When facing muscle tissue, the electrodes were apt to detect myopotentials and were susceptible to baseline drift. The present invention minimizes myopotentials and allows the device to be implanted in a variety of subcutaneous or submuscular locations of a patient's thorax by providing maximum electrode separation and minimal signal variation due to various orientation of an IMD within a surgically-created pocket because the electrodes are placed on the surround shroud in such a way as to maximize the distance between electrode pairs. The shroud provides insulation from the typically metallic IMD casing due to the insulative properties of the compliant shroud and recesses where the electrodes are mechanically coupled. The electrode placement maintains a maximum and equal distance between the electrode pairs. Such spacing with the four-electrode embodiment maintains maximum average signal due to the fact that the spacing of the two vectors is equal and the angle between these vectors is 90°, as known in the art and as predicted via mathematical modeling. Such orthogonal spacing of the electrode pairs also minimizes signal variation. An alternate three-electrode embodiment provides the electrodes arranged within the surround shroud in an equilateral triangle along the perimeter of the implanted pacemaker. Vectors in this embodiment can be combined to provide adequate sensing of cardiac signals.

With respect to the elongated conductor coupling the planar electrodes to operative circuitry within an IMD, the assembly can comprise a unitary member stamped from a plate of conductive material such as titanium. In one embodiment the unitary member comprises a pre-shaped partially serpentine workpiece having a slightly curvilinear (i.e., substantially planar) major plate portion, a transition portion, and a partially serpentine portion adapted to cooperate with the configuration of the pre-configured conductor pathway.

For mass production of assemblies according to the invention a unique electrode piecepart can be fabricated for each unique conductor pathway and recess shape and configuration (including any of the variety of diverse mechanical interlocking features described hereinabove). Besides manufacturing processes such as metal stamping, the metallic electrode member(s) can be fabricating using electron discharge machining (EDM), laser cutting, or the like. It is desirable that the electrode assemblies are pre-configured (at least in a two-dimensional (2D) manner) so that little or no mechanical deformation or bending is required to fit each assembly into a shroud member. In addition, due to pre-configuring the parts the bends occur in a highly predictable manner and retain relatively little, if any, energy due to the spring-constant of the metal used to form the parts. In the event that electrical insulation or a dielectric layer becomes necessary or desirable, the major elongated portion of an electrode assembly can be coated with an insulative material such as paralyne or similar while the portions of the assembly likely to contact body fluid can be coating with diverse coatings pursuant to various embodiments of the invention.

Electrode assemblies according to the invention can be used for chronic or acute EC-EGM signal sensing collection and attendant heart rate monitoring, capture detection, arrhythmia detection, and the like as well as detection of myriad other cardiac insults (e.g., ischemia monitoring using S-T segment changes, pulmonary edema monitoring based upon impedance changes).

In addition, the surface of the electrode can be treated with one or more electrode coatings to enhance signal-conducting, de- and re-polarization sensing properties, and to reduce polarization voltages (e.g., platinum black, titanium nitride, titanium oxide, iridium oxide, carbon, etc.). That is the surface area of the electrode surfaces may be increased by techniques known in the art. and/or can be coated with such materials as just described and equivalents thereof. All of these materials are known to increase the true electrical surface area to improve the efficiency of electrical performance by reducing wasteful electrode polarization, among other advantages.

Many of the embodiments of the inventive electrodes herein can provide a continuous electrical path free of welds or bonds on a portion of the planar electrode, the transition portion, the elongated conductor or the distal tip portion. Moreover, the electrode assembly according to the invention anchors to a shroud member free of any chemical or adhesive bonding materials that can cause excursions due to electro-active specie release to the electrode surface or portions thereof.

These and other advantageous aspects of the invention will be appreciated by those of skill in the art after studying the invention herein described, depicted and claimed. In addition, persons of skill in the art will appreciate insubstantial modifications of the invention that are intended to be expressly covered by the appended claims.

DETAILED DESCRIPTION OF THE DRAWINGS

Figure 1:
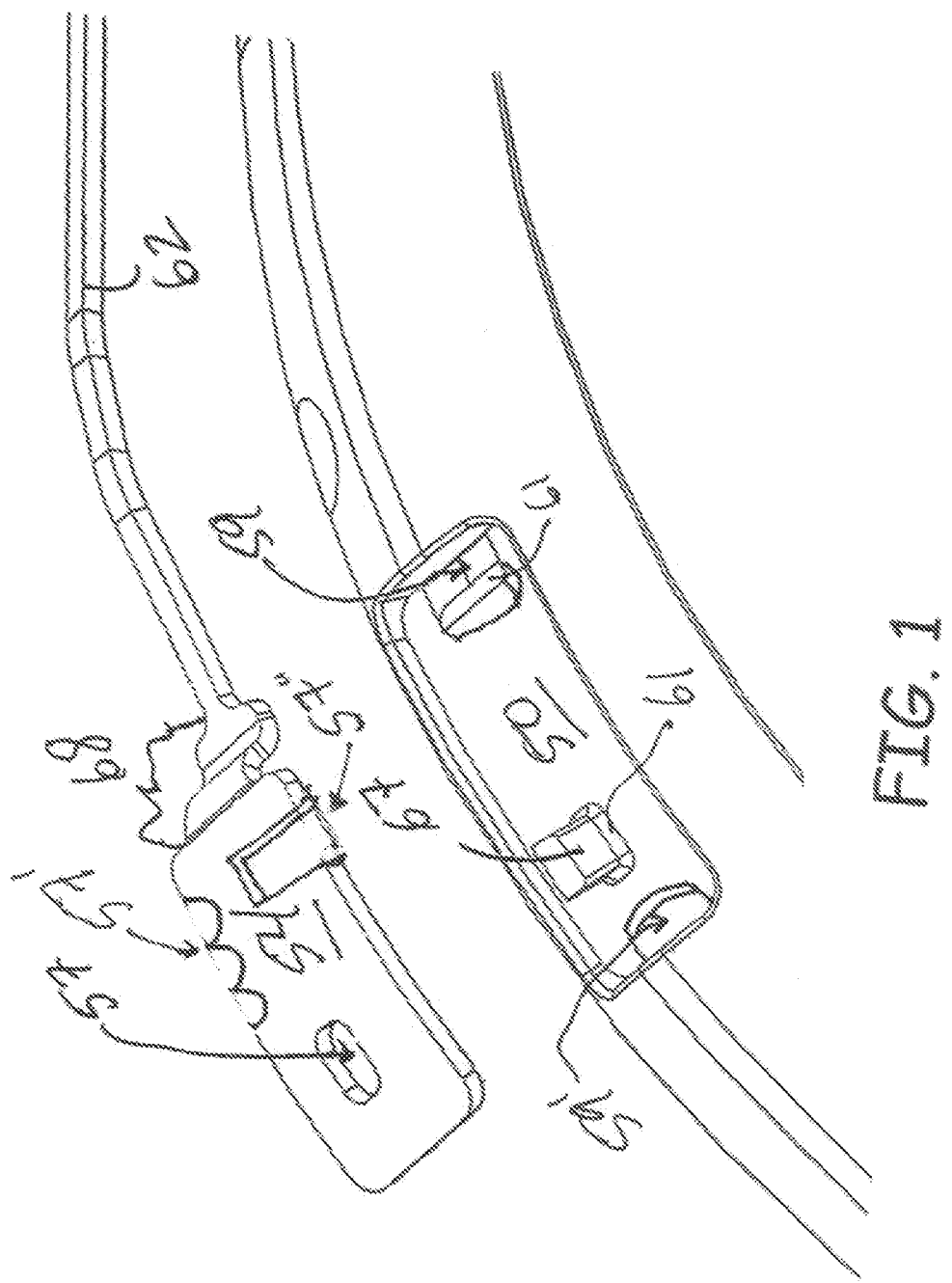
FIG. 1 is an exploded view depicting an exemplary electrode adjacent an electrode receiving recess according to one embodiment of the invention.

FIG. 1 is an exploded view depicting an exemplary substantially planar electrode 54 according to the invention disposed adjacent an electrode receiving recess (or aperture) 50 according to one embodiment of the invention. Also depicted in FIG. 1 is an optional aperture 57 formed in the electrode 54 for receiving the protrusion 67 having a spacer member 61 disposed adjacent the major surface of recess 50. The spacer member 61 functions as a mechanical stop thus assuring a minimum spacing between the electrode 54 and the recess 50. Recess 50 is depicted with optional opposing apertures 59,59' one of which can be used to receive and, preferably, retain a conductive transitional portion 68 (and thus elongated conductor 62). The other aperture 59,59' thus functions as a source of fluid flow. In combination the protrusion 67 and the aperture 57 and the transitional portion 68 and the aperture 59 (or 59') provide two discrete fixation locations for the electrode 54 both of which can be used to maintain a desired minimum separation between the electrode 54 and recess 50. For example the apertures 59,59' (or additional apertures) can be located at any portion of the periphery or major part of the recess 50 to provide a discrete retaining force and/or to promote fluid flow. In addition to or in lieu of the foregoing one of more protrusion members 67 can provide other discrete fixation and/or mechanical stop (spacer) locations for the electrode 54. Also depicted are notch 57' and slot 57" which are formed in the electrode 54 to promote fluid ingress and egress according to the invention.

The protrusion 67 can comprise a unitary member adapted to receive an ultrasonic bonding horn to thus form a rivet-like enlarged head portion to increase the fixation of the electrode 54 and/or can comprise a split member which expands after the electrode 54 is fully mounted. Such a split member can include an enlarged head portion for retaining the electrode (with or absent ultrasonic bonding of same), such as a frustoconical portion. Spacer 61 can comprise a discrete step or enlarged portion configured to support the electrode 54 at a desired elevation relative to the major surface of recess 50.

As known in the art of ultrasonic bonding an ultrasonic head couples to the protrusion 67 which can comprise a thermoplastic or resin-based material and the material quickly deforms; in this case, the material deforms to provide additional mechanical fixation to the substantially planar electrode 54. The operative head of the ultrasonic head can be configured to only impinge upon the protrusion 67 and not with any surrounding part of the shroud 48 (e.g., the edges of the recess 50, etc.). While not specifically depicted herein, in this aspect of the invention the head comprises an effective head portion adapted specifically for producing a weld nugget on the upper portion of protrusion 67. Issued U.S. Pat. No. 6,205,358 entitled "Method of Making Ultrasonically Welded, Staked or Swaged Components in an Implantable Medical Device" and assigned to Medtronic, Inc. describes and depicts some aspects of ultrasonic welding and the entire contents of the '358 patent are hereby incorporated herein. Also, U.S. Pat. No. 6,768,128 entitled "Ultrasonic-Welding Apparatus, Optical Sensor and Rotation Sensor for the Ultrasonic-Welding Apparatus is hereby incorporated herein by reference.

Figure 2:
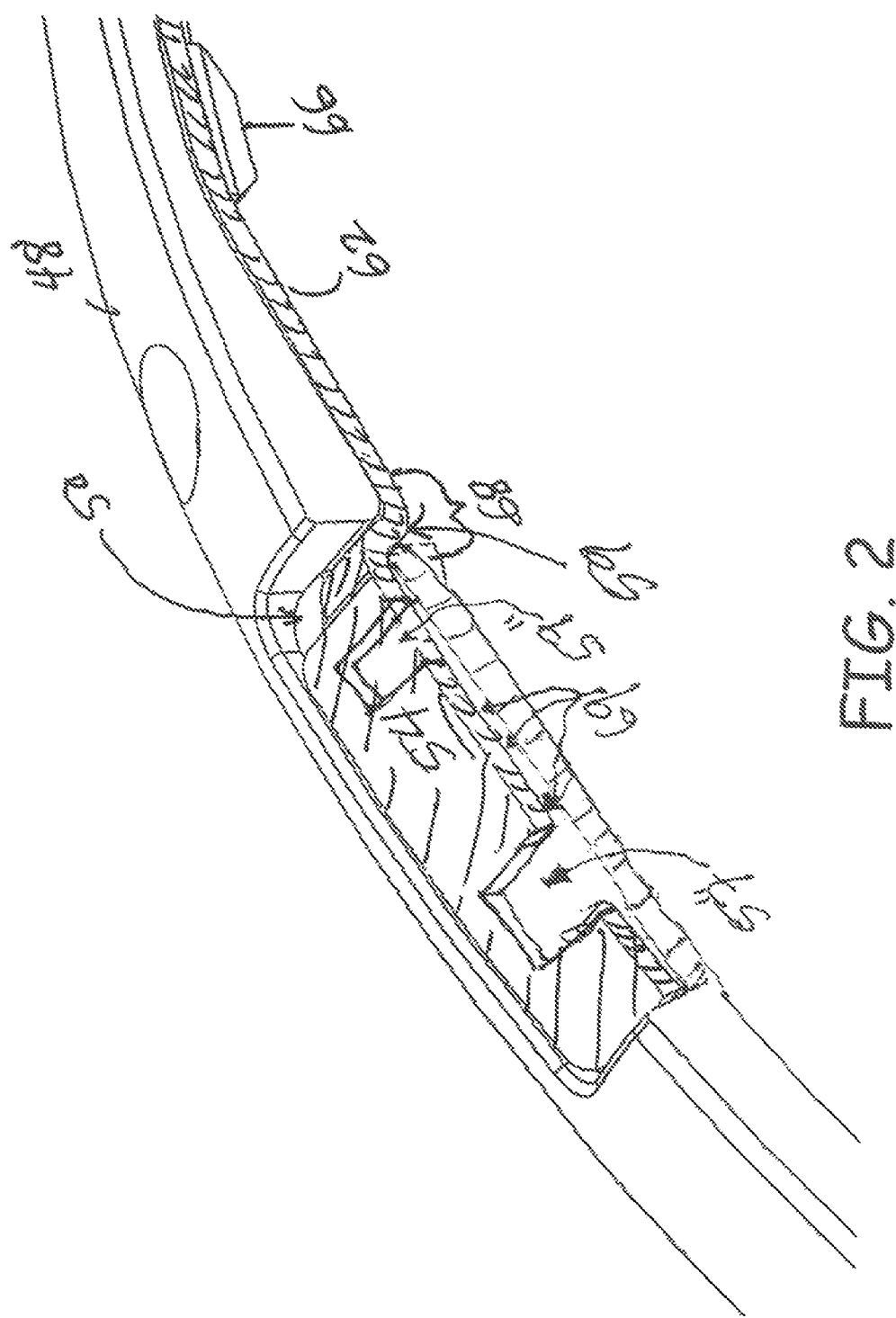
FIG. 2 depicts in perspective view a cross-sectional portion of an electrode-receiving recess having an electrode coupled therein according to one embodiment of the invention.

FIG. 2 depicts in perspective view a cross-sectional portion of an electrode-receiving recess 50 having an electrode 54 coupled therein according to one embodiment of the invention. In the depicted embodiment the recess 50 is devoid of the protrusion (67) as just described and instead a pair of slots 57" are distributed over the major planar portions of the electrode 54. A transitional portion 68 of the electrode assembly is shown effectively interlocked with aperture 59 and since the relative size of electrode 54 is smaller than the recess 50, another fluid pathway is provided (indicated by arrow 50) through aperture 59. In the depicted embodiment opposing surfaces of the aperture 59 mechanically cooperate with surface portions of the transitional portion 68 to effectively provide three-dimensional (3D) mechanical support thereto. An open space between the electrode 54 and the recess 50 is indicated by arrows 69 which further promotes free circulation of fluids therethrough as previously described.

Figure 3:
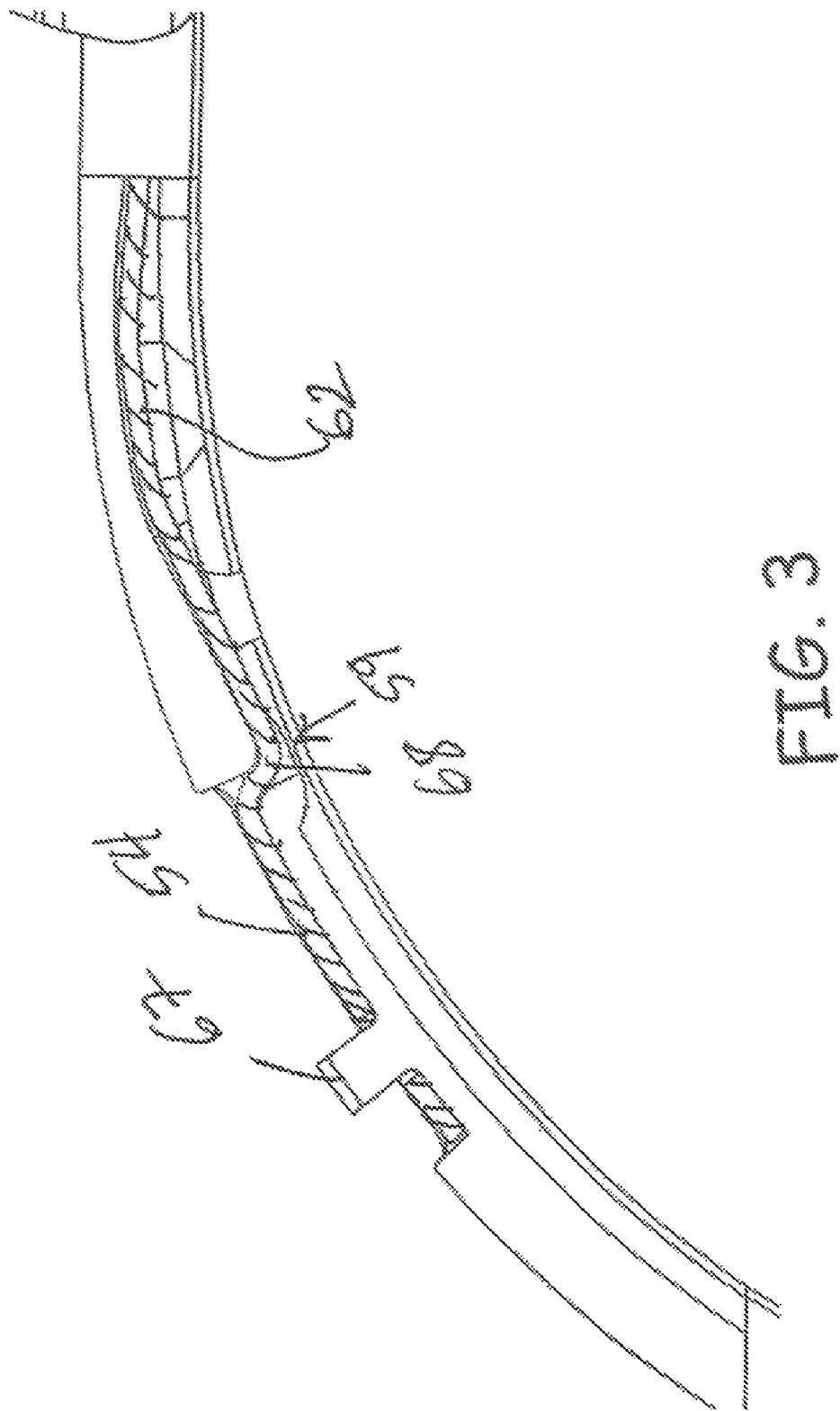
FIG. 3 is an elevational view in cross-section of the electrode-receiving recess having an electrode coupled therein according to one embodiment of the invention.

Referring now to FIG. 3, an elevational view in cross-section of the electrode-receiving recess 50 having an electrode 54 coupled therein according to one embodiment of the invention is illustrated. In this view at least two of the 3D mechanical support features of the aperture 59 is depicted. Of course, other shapes and geometries can be effectively utilized to provide such mechanical support, and to the extent that a protrusion member 67 retains the electrode within the recess 50 then the retentions requirements for the interlocking portions 59,68 can be relaxed.

Figure 4:
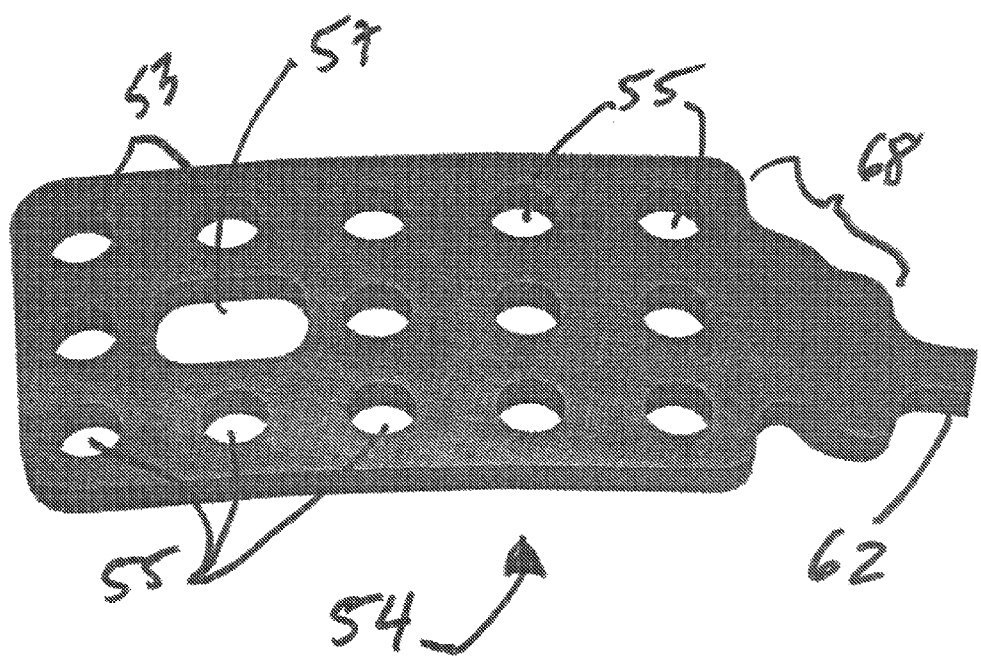
FIGS. 4-6 are perspective views of alternative embodiments of an electrode according to the invention.
Figure 5:
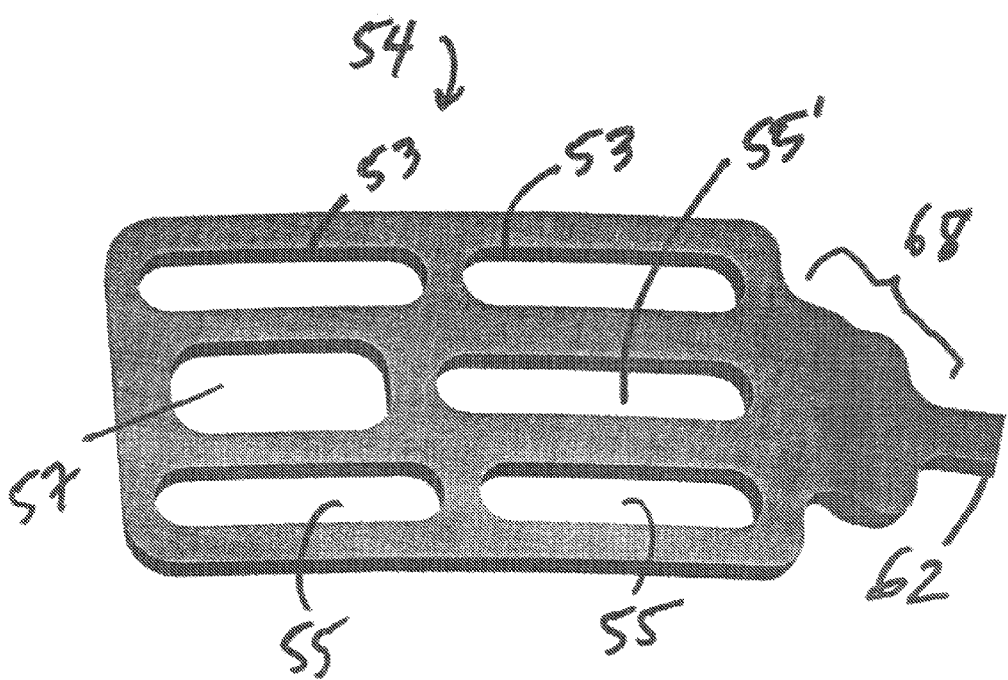
Figure 6:
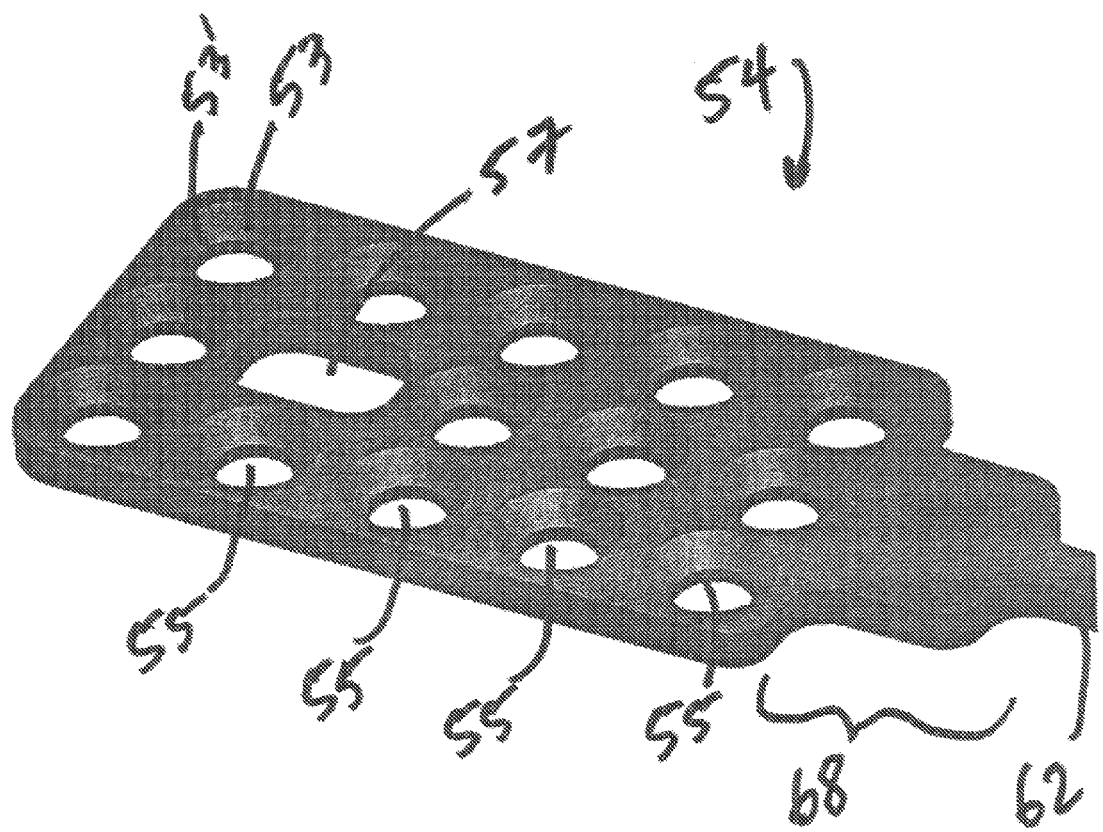

FIGS. 4-6 are perspective views of alternative embodiments of an electrode according to the invention. Referring to FIG. 4, a substantially planar electrode 54 is depicted. The electrode 54 includes a series of apertures 55 coupling major opposing surfaces of the electrode 54 to thereby promote circulation of fluids therearound. As depicted the apertures 55 are configured in a regular array, with the exception of aperture 57 which can be optionally utilized to mechanically couple the electrode with an boss or the like (e.g., a protrusion 67 depicted in FIGS. 1-3) to the shroud (not depicted in FIG. 4). Of course, the apertures 55 can be arranged in a random or regular configuration.

Also, the apertures 55 are depicted with substantially parallel interior surfaces but the interior surfaces 53 can be configured in a wide variety of ways (e.g., convex, concave, slanted, curved, etc.). Also while the depicted apertures 55 appear to have a uniform shape (i.e., circular) the apertures 55 can be designed to have arbitrary and/or different shapes.

Referring now to FIG. 5, an alternative embodiment of the invention is depicted that is similar to the embodiment depicted in FIG. 4. However, four of the apertures 55 appear very similar in size and shape while one aperture 55' has a different size and shape. Both apertures 55,55' include substantially parallel interior surfaces 53. And the electrode 54 includes an optional aperture 57 for mechanically coupling the electrode to a shroud according to certain aspects of the invention.

FIG. 6 illustrates yet another alternate embodiment wherein the apertures 55 are distributed over the surface of electrode 54 in an array, with the exception of optional aperture 57. However, the apertures 55 include interior surface portions 53,53' of which surface portion 53 is non-parallel while interior surface portion 53' is parallel. The electrode 54 and thus the apertures 55 of FIG. 6 could be inverted from the embodiment depicted so that the major opening (defined by the outer periphery of surface 53) abuts the shroud and thus tends to drain any material(s) disposed therebetween.

Of course, the electrodes 54 can be fabricated out of any appropriate material, including without limitation tantalum, tantalum alloy, titanium, titanium alloy, platinum, platinum alloy, or any of the tantalum, titanium or platinum group of metals whose surface may be treated by sputtering, platinization, ion milling, sintering, etching, or a combination of these processes to create a large specific surface area. Also as noted herein, an electrode can be stamped, drawn, laser cut or machined using electronic discharge apparatus. Some of the foregoing might require de-burring of the periphery of the electrode or alternately any sharp edges due to a burr can be coupled facing toward the corresponding recess in the shroud member thereby minimizing likelihood of any patient discomfort post-implant while further reducing complexity in the fabrication of assemblies according to the invention. The electrodes can be coated or covered with platinum, a platinum-iridium alloy (e.g., 90:10), platinum black, titanium nitride or the like.

Accordingly, a number of embodiments and aspects of the invention have been described and depicted although the inventors consider the foregoing as illustrative and not limiting as to the full reach of the invention. That is, the inventors hereby claim all the expressly disclosed and described aspects of the invention as well as those slight variations and insubstantial changes as will occur to those of skill in the art to which the invention is directed. The following claims define the core of the invention and the inventors consider said claims and all equivalents of said claims and limitations thereof to reside squarely within their invention.

The invention claimed is:

1. A subcutaneous cardiac activity sensing shroud, comprising:
   a shroud member for location adjacent at least a part of the peripheral portion of a housing for an implantable medical device (IMD), said shroud member including a recessed region having a major surface and surrounding edges; and
   a substantially flat electrode located within the recessed region between the edges and having a surfaces facing and spaced from the major surfaces of the recessed region thereby defining a cavity therebetween;
   wherein the electrode includes one of: an aperture, a notch, and a slot extending therethrough adapted to promote flow of body fluid through the cavity.

2. A shroud according to claim 1, wherein said shroud member comprises a resilient material.

3. A shroud according to claim 1, further comprising at least one aperture is located over the recessed region.

4. A shroud according to claim 1, further comprising an elongated conductor coupled to the electrode.

5. A shroud according to claim 4, wherein the elongated conductor comprises an integrally formed structure with the electrode.

6. A subcutaneous cardiac activity sensing shroud, comprising:
   a shroud member for location adjacent at least a part of the peripheral portion of a housing for an implantable medical device (IMD), said shroud member including a recessed region having an outwardly facing major surfaces and surrounding edges; and
   a substantially flat electrode located within the recessed region between the edges and having a substantially flat surfaces inward and spaced from the major surfaces of the recessed region and separated from the major surfaces by an open cavity therebetween;
   wherein the electrode includes one of: an aperture, a notch, and a slot extending therethrough adapted to promote flow of body fluid into the cavity.

7. A shroud according to claim 6, wherein said shroud member comprises a resilient material.

8. A shroud according to claim 6, further comprising a mechanical stop maintaining the electrode at a present elevation relative to the major surfaces of the recessed region.

9. A shroud according to claim 6, wherein the at least one aperture is located over the recessed region.

10. A shroud according to claim 6, further comprising an elongated conductor couple to the electrode.

11. A shroud according to claim 10, wherein the elongated conductor comprises an integrally formed structure with the electrode.

12. A subcutaneous cardiac activity sensing shroud, comprising:
   a shroud member for location adjacent at least a part of the peripheral portion of a housing for an implantable medical device (IMD), said shroud member including a recessed region having an outwardly facing major surfaces and surrounding edges; and
   a substantially flat electrode located within the recessed region between the edges and spaced from the major surfaces of the recessed region and separated from the by an open cavity therebetween;
   wherein the electrode includes one of: an aperture, a notch, and a slot extending therethrough adapted to promote flow of body fluid into the open cavity.

13. A shroud according to claim 12, wherein said shroud member comprises a resilient material.

14. A shroud according to claim 12, further comprising a mechanical stop maintaining the electrode at a present elevation relative to the major surface of the recessed region.

15. A shroud according to claim 12, wherein the at least one aperture is located over the recessed region.

16. A shroud according to claim 12, further comprising an elongated conductor coupled to the electrode.

17. A shroud according to claim 16, wherein the elongated conductor comprises an integrally formed structure with the electrode.

* * * * *

UNITED STATES PATENT AND TRADEMARK OFFICE
CERTIFICATE OF CORRECTION

| | | |
|---|---|---|
| PATENT NO. | : 7,925,322 B2 | Page 1 of 1 |
| APPLICATION NO. | : 11/380811 | |
| DATED | : April 12, 2011 | |
| INVENTOR(S) | : Stancer et al. | |

It is certified that error appears in the above-identified patent and that said Letters Patent is hereby corrected as shown below:

Col. 9/Line 14. Error reads as "surfaces"; Correction to Patent Should be "surface".

Col. 9/Line 22. Error reads as ",further compristing..."; Correction to Patent Should be ", wherein the...".

Col. 9/Line 35. Error reads as "surfaces"; Correction to Patent Should be "surface".

Col. 9/Line 38. Error reads as "surfaces"; Correction to Patent Should be "surface".

Col. 9/Line 39. Error reads as "surfaces"; Correction to Patent Should be "surface".

Col. 10/Line 8. Error reads as "surfaces"; Correction to Patent Should be "surface".

Col. 10/Line 11. Error reads as "couple"; Correction to Patent Should be "coupled".

Col. 10/Line 20. Error reads as "surfaces"; Correction to Patent Should be "surface".

Col. 10/Line 24. Error reads as "surfaces"; Correction to Patent Should be "surface".

Signed and Sealed this
Thirteenth Day of March, 2012

David J. Kappos
*Director of the United States Patent and Trademark Office*